United States Patent [19]

Buttram et al.

[11] Patent Number: 5,714,688
[45] Date of Patent: Feb. 3, 1998

[54] EMAT MEASUREMENT OF DUCTILE CAST IRON NODULARITY

[75] Inventors: Jonathan David Buttram, Bedford; Wayne Meredith Latham, Forest, both of Va.

[73] Assignee: The Babcock & Wilcox Company, New Orleans, La.

[21] Appl. No.: 316,309

[22] Filed: Sep. 30, 1994

[51] Int. Cl.$^6$ .............................. G01N 29/18; G01N 29/00
[52] U.S. Cl. .............................. 73/597; 73/643; 73/598
[58] Field of Search .............................. 73/597, 643, 598, 73/602

[56] References Cited

U.S. PATENT DOCUMENTS

| | | | |
|---|---|---|---|
| 3,603,136 | 9/1971 | Diamond et al. | 73/67.8 |
| 3,690,155 | 9/1972 | Eichler | 73/597 |
| 3,774,444 | 11/1973 | Kent | 73/67.6 |
| 3,844,163 | 10/1974 | Di Leo | 73/67.5 |
| 3,848,460 | 11/1974 | Bantz et al. | 73/67.5 |
| 4,114,455 | 9/1978 | Walker | 73/597 |
| 4,307,616 | 12/1981 | Vasile | 73/643 |
| 4,348,903 | 9/1982 | Sato et al. | 73/643 |
| 4,568,388 | 2/1986 | Dremann et al. | 75/130 |
| 5,035,143 | 7/1991 | Latimer et al. | 73/598 |
| 5,172,591 | 12/1992 | Bohon | 73/151 |
| 5,216,921 | 6/1993 | Tsuboi | 73/579 |
| 5,299,458 | 4/1994 | Clark, Jr. et al. | 73/597 |

OTHER PUBLICATIONS

G.J. Parkinson et al., "Non–Contact Ultrasonics", Jul. 1977, pp. 178–184.

Beissner, R.E., "Electromagnetic–Acoustic Transducers A Survey of the State of the Art", Jan., 1976.

Metals Handbook, 9$^{th}$ Edition, ©1989, ASM International, pp. 532–35.

Henderson, H.E., "Ultrasonic Velocity Technique for Quality Assurance", Foundry Trade Journal v136 n 2985, Feb. 21, 1974, pp. 203–09.

Rickards, P.J. "Progress in Guaranteeing Quality Through Non–Destructive Methods of Evaluation." UK Official Exchange Paper, The Foundryman International, pp. 196–209, 1987.

Primary Examiner—Hezron E. Williams
Assistant Examiner—Nashmiya Ashraf
Attorney, Agent, or Firm—Robert J. Edwards; Eric Marich

[57] ABSTRACT

A method of examining a ductile iron casting to determine a percent of nodularity present in the casting uses an electromagnetic acoustic transducer (EMAT) system to determine a time-of-flight of an ultrasonic shear wave pulse transmitted through the casting at a selected location, from which a velocity of sound in the casting can be determined. The ultrasonic shear wave pulse created and sent through the casting experiences several internal reflections within the casting, and the absolute delay time for both second, $T_{DELAY1}$, and third, $T_{DELAY2}$, multiple reflections are used to determine the time, $T_{DELTA}$, required for the ultrasonic pulse to travel through twice the thickness, t, of the casting at said location. The velocity, $V_{SHEAR}$, of the ultrasonic shear wave pulse through the casting is calculated from $T_{DELTA}$ and a measurement of the thickness, t, of the casting at the location being inspected. The percent of nodularity of the casting is determined from a pre-established relationship between the calculated shear wave velocity, $V_{SHEAR}$, and the percent of nodularity for ductile cast iron.

8 Claims, 3 Drawing Sheets

FIG. 5
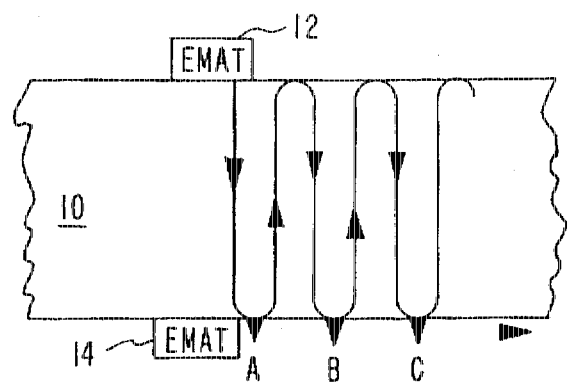
FIG. 6
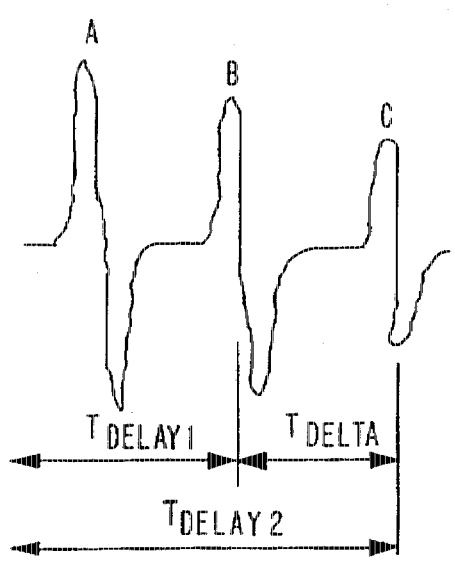
FIG. 7
| Part Number | $T_{DELAY1}$ (sec) | $T_{DELAY2}$ (sec) | $T_{DELTA}$ (sec) | Thickness (inches) | Shear Wave Velocity (in/sec) | Long Wave Velocity (in/sec) |
|---|---|---|---|---|---|---|
| #1 | 14.80 E-06 | 26.05 E-06 | 11.25 E-06 | 0.6815 | 1.212 E05 | 2.183 E05 |
| #2 | 14.80 E-06 | 26.00 E-06 | 11.20 E-06 | 0.6819 | 1.218 E05 | 2.190 E05 |
| #4 | 14.60 E-06 | 25.89 E-06 | 11.29 E-06 | 0.6891 | 1.221 E05 | 2.188 E05 |

EMAT MEASUREMENT OF DUCTILE CAST IRON NODULARITY

FIELD AND BACKGROUND OF THE INVENTION

The present invention relates, in general, to nondestructive examination techniques used to characterize the properties of castings and, in particular, to a method of examining ductile iron castings using an electromagnetic acoustic transducer (EMAT) system to determine a percent of nodularity present in such castings.

Ductile iron is cast iron in which the graphite is present in tiny balls or spherulites instead of flakes (as in gray iron) or compacted aggregates (as in malleable iron). Castings of ductile iron are used extensively in the automotive and heavy equipment industries for engine, brake, suspension, and steering components. All safety related items are required to undergo proof testing to insure proper strength.

As discussed at page 532 in Volume 17-Nondestructive Evaluation and Quality Control, of the *Metals Handbook*, 9th Edition, ©1989 by ASM International, both the velocity of ultrasonic transmission and the resonant frequency of a casting can be related to the modulus of elasticity. In cast iron, the change from flake graphite to nodular graphite is related to an increase in both modulus of elasticity and strength; therefore, ultrasonic velocity or resonant frequency measurement can be employed as a guide to nodularity, strength, and other related properties of the casting. Because the microscopic estimation of nodularity is a subjective measurement, these other nondestructive examination methods may provide a better guide to some properties, provided that the matrix remains constant. FIG. 1 of the present disclosure is shown at page 532 of the *Metals Handbook*, supra, and illustrates how ultrasonic velocity may vary with graphite nodularity.

H. E. Henderson's article titled "Ultrasonic Velocity Technique for Quality Assurance", appearing in the *Foundry Trade Journal*, Feb. 21, 1974, at pages 203–208, describes a non-destructive ultrasonic velocity technique employed for the measurement of nodularity of ductile iron castings. As discussed therein, while sound has relatively constant velocity through aluminum, steel and other homogeneous materials, cast iron, however, is non-homogeneous and the velocity at which ultrasonic sound waves are transmitted through cast iron structures is affected by the size, shape and distribution of the graphite and according to whether the casting has been subjected to heat treatment. If the sound velocity can be measured accurately and the size and distribution of the graphite is relatively constant, then the value of sound velocity will vary according to the shape of the graphite for each condition, i.e., as-cast, high-temperature heat treatment, low-temperature heat treatment, etc. The sound velocity will be greatest when the structure contains perfect graphite spheroids in the as-cast condition. FIG. 2 of the present disclosure shows such a longitudinal velocity/ nodularity relationship as presented in the H. E. Henderson article, supra.

Henderson discusses two approaches using the ultrasonic velocity technique. The first, shown in FIG. 1 of the article, uses only one transducer to measure transit time while mechanical thickness is determined electromechanically. The second method, shown in FIG. 2 of the article, requires two transducers at perfect acoustical alignment. Signals from these transducers are used to update, through a temperature compensation circuit, the water path distance. In order to utilize the latter technique, the part is placed between the transducers and all are immersed in water. The two water paths and the ultrasonic transit time through the part are measured and the ultrasonic velocity is calculated and displayed on a digital readout.

The graphite in a gray cast iron, as shown in FIG. 3 of Henderson's article, offers great resistance to the passage of sound waves and the velocity would be low (approximately 170,000 inches per second). On the other hand, the graphite in ductile iron, as shown in FIG. 4 of Henderson's article, would offer less resistance to the passage of sound waves and the velocity would be higher (approximately 225,000 inches per second). From previous data, it had been established that if the structure of a ductile iron casting had a nodularity of 90%, then the mechanical properties may be predicted by the Brinell hardness number. It thus followed that if the sonic velocity can be measured to establish the nodularity, then the mechanical properties can be predicted. As shown in FIG. 7 of the Henderson article, castings which must meet a specification of 80% minimum nodularity required a minimum velocity of 223,000 inches per second for as-cast castings and 217,000 inches per second for heat-treated castings. At the time of the article, circa 1973–74, it was not believed that the ultrasonic velocity test was sufficiently accurate enough to recommend it as a replacement of the known tensile test methods, but that the relationship was close enough that the ultrasonic testing technique could be used to qualify castings when there was some question as to individual strength.

The usefulness of conventional ultrasonic techniques for ductile iron velocity measurement is thus well established. Various methods and apparatus employing the concept that ultrasonic velocity can be related to nodularity have been patented. Diamond (U. S. Pat. No. 3,603,136) discloses a method and apparatus for determining the percent nodularity of a workpiece as a function of the speed of ultrasonic sound through the workpiece. According to a first embodiment, this is achieved by positioning the workpiece at a predetermined distance from an electro-acoustic transducer and in a second embodiment by positioning the casting between two electro-acoustic transducers which are spaced at a predetermined distance. The invention asserts that the prior art technique of making actual thickness measurements of the casting, usually by manual methods, is dispensed with and that the method and apparatus can be used to determine the percent nodularity of a workpiece regardless of the workpiece thickness.

As disclosed in Diamond, the workpiece or casting 10 is immersed in water 20 and has first and second surfaces 12 and 14 respectively. An ultrasonic pulse is generated by a crystal 26 immersed in the water 20 and has sufficient energy so that it will pass through both the first and second surfaces 12 and 14. First and second back reflections 42, 44 are produced at these surfaces and crystal 26 generates signals upon reception of each back reflection. An oscilloscope 38 displays the transmitted pulse 40 and the first and second back reflections 42, 44. The time between the display of the second and third pulses 42, 44 is thus the total time required for the ultrasonic impulse to travel from the first surface 12 to the second surface 14 and for the second back reflection impulse to travel from the second surface 14 to the first surface 12. If the crystal 26 is positioned a predetermined distance K away from the second surface 14, the actual thickness M of the casting can essentially be eliminated from subsequent calculations which then determine the velocity of sound in the workpiece solely as a function of the time between the display of the first and second pulses and the time between the display of the second and third pulses.

P. J. Rickards, in a paper entitled "Progress in Guaranteeing Quality Through Nondestructive Methods of Evaluations", appearing in the *Foundryman International*, April 1988, pages 196–209, discusses various methods used to evaluate casting structure, starting at page 204 thereof. Rickards acknowledges that ultrasonic velocity measurements are usually made using meters which measure the time taken for sound to travel through a section of a component, and that micrometers or calipers have been used to measure thickness. A system is discussed which eliminated the need to measure thickness by employing a double ultrasonic probe having both longitudinal and shear wave transducers. The times taken for the pulses to be reflected from the back walls of the casting are measured and, by comparison, velocity was accurately and directly calculated. Other automated methods of velocity measurement are also discussed in the Rickards paper, and include those which employ double probe transmission in water. Again, the velocity of sound in the material is calculated and compensation can be made for variations in thickness and water temperature. A computer automatically performs these calculations and can also provide an indication of whether or not the casting is acceptable. Other methods, including measurement of the resonant frequency of castings to assess their graphite structures, are also mentioned. Resonant frequency (sonic) testing was stated to be well suited for long runs of castings as calibration is required for each casting design. The advantage of this technique is that properties of the whole casting are assessed rather than the evaluation being made in a specified test area. Other developments in sonic testing include analysis of the full frequency spectrum of the resonating castings, induced by striking the castings themselves. Frequencies generated are picked up with a microphone, analyzed and fed to a computer. Resonant peaks and amplitudes in the frequency spectrum are compared with stored data for similar castings of known acceptable quality. Some claims have been made that these computer-assisted techniques not only identified defective castings but also indicated whether the casting has a poor nodular graphite structure, contained carbide, cracks or shrinkage, or deviated from dimensional specifications.

Kent (U.S. Pat. No. 3,774,444) discloses a system for determining the sonic velocity and related characteristics of a sample of solid material such as malleable or ductile iron. The system includes a portable hand-carried unit having means engagable with opposite surface portions of the sample, sensing means for developing an electrical characteristic which varies as a function of the distance between the engagement means, and ultrasonic transducer means for transmitting waves through the sample from one surface portion to the other and back again. The particular hand-carried units disclosed appear similar to those discussed earlier in Henderson, supra.

Di Leo (U.S. Pat. No. 3,844,163) discloses an ultrasonic nondestructive testing system for measuring the velocity at which ultrasonic energy propagates through a material. It is particularly adapted to be used on a material such as nodular cast iron for ascertaining the percentage of nodularity. A pair of search units are provided for propagating ultrasonic energy towards the opposites sides of a workpiece and receiving such energy therefrom. A computer is provided for measuring the various time delays resulting from the ultrasonic energy propagating through the workpiece and computing the velocity of the ultrasonic energy in the workpiece. The particularly disclosed system is said to eliminate adverse affects of temperature variations upon velocity, as well as to address the fact that various typical casting surfaces are rough and irregular and thus the dimensions may vary over a substantial and unpredictable range. In particular, it is stated in Di Leo that very frequently errors in measuring the distance have been equal to or in excess of the variations which may be expected in the velocity of the ultrasonic energy.

Bantz et al. (U.S. Pat. No. 3,848,460) also discloses a method of measuring the velocity of sound in a workpiece using transmit and receive ultrasonic transducers spaced a predetermined distance apart from each other in a liquid bath. Automatic and continuous updates of the velocity measurement are made for changes in temperature and contamination of the liquid.

Dremann et al. (U.S. Pat. No. 4,568,388), while being drawn to a particular type of cast iron, is of interest in its discussion at col. 4, lines 51–62 of the various ranges of ultrasonic velocities descriptive of various types of cast irons.

Tsuboi (U.S. Pat. No. 5,216,921) discloses a method and apparatus for detecting defects and different-hardness portions of an object with protrusions, and employs spectral analysis of vibrations applied to the test object. This method and apparatus relies upon the principle that defects in protrusions cause vibrations to be transmitted through paths that bypass such defects. Various spectral energy peaks are associated with both the paths of natural vibrations and the bypassing paths. Two separate energy peaks identify regions having defects.

As indicated by the aforementioned references, generation of ultrasonic waves is achieved primarily by some form of electromechanical conversion, usually piezoelectricity. This highly efficient method of generating ultrasound has a primary disadvantage, in that it requires a fluid couplant to mechanically transfer sound generated by the transducer into and out of the component being tested. The test object must be covered with a thin layer of fluid (i.e., couplant) or immersed in liquid which complicates testing and often reduces the inspection rate. In some cases, the test is impossible because of this requirement. Couplant cleanup can be a significant problem in certain applications, and post-test corrosion of castings has traditionally been a cause of part rejection. In addition, the actual length of time required to actually "wet" the parts being inspected can significantly delay the speed of the overall manufacturing/inspection process. It is thus evident that an ultrasonic technique for determining cast iron nodularity which does not rely on a couplant has many advantages to offer in practical applications.

A technique not needing a fluid couplant has been developed within approximately the last twenty years, and employs devices known as electromagnetic acoustic transducers (EMATs). Electromagnetic Acoustic Transducers (EMATs) are the basis of a non-contact ultrasonic inspection method which requires no fluid couplant because the sound is produced by an electromagnetic acoustic interaction within the material. This technique can be used to eliminate the couplant which complicates testing procedures, slows inspection rates, and can introduce errors into the measurement.

Clark, Jr. et al. (U.S. Pat. No. 5,299,458) discloses a process for ultrasonically evaluating the formability of metallic sheets which employs EMATs to measure ultrasonic velocities at various angles to the rolling direction of the sheet specimens. An ultrasonic correlation parameter is calculated from these measurements, compared against formability indexes obtained by destructive examination of other specimens, and used with the previous calculated correlation to ascertain the formability index for the working sample.

Bohon (U.S. Pat. No. 5,172,591) discloses a load measuring system used to determine the loadings in an oil well sucker rod. Measurements are taken in both the loaded and unloaded portions of the rod and used to indicate the dynamic load. Acoustic transmitters, of a traditional piezoelectric type, are used in the preferred embodiment, but the patent at col. 5 indicates that problems with firm coupling and the use of couplant can be overcome by using EMATs. The patent states that EMATs are primarily effective for inducing a waveform having particle motion normal to the metal surface such as shear waves or surface waves and that, if desired, such EMATs could be used in place of the more typical transducers, provided the system was otherwise calibrated for the appropriate resulting waveform.

Latimer et al. (U.S. Pat. No. 5,035,143) is drawn to a method for ultrasonically detecting creep swelling in tubular members such as fossil utility steam lines and headers. Ultrasonic surface waves are propagated around the pipe in a circumferential direction and the transit time is measured using pulse overlap techniques and an oscilloscope. Circumferential dimensions are obtained by multiplying the transit time by the known Raleigh velocity of sound in the tubular member. EMATs may be employed for generating the ultrasonic waves.

Finally, Vasile (U.S. Pat. No. 4,307,616) discloses a signal processing technique for ultrasonic inspection using EMATs. The patent is directed primarily to developing an improved technique for processing the signals from an EMAT-equipped ultrasonic testing system. The invention is drawn to the problems of overcoming the inherently low level of signal generation when EMATs are employed, and their sensitivity to local inhomogeneities in the materials under inspection. Additional deficiencies identified were the presence of excessive levels of random electronic noise, electronic machinery noise and grain noise arising from the material being tested. The device has a signal generator which produces a reference wave form and a multiplier for combining the electrical signal and a reference waveform which is then integrated to produce a combined signal.

A simple EMAT consists of a coil of wire and a magnet. A strong magnetic field is produced at the surface of the conductor by a permanent magnet or an electromagnet. Eddy currents are induced in the surface of the conductor by the coil which is driven at high frequency by an oscillator. The Lorentz force resulting from the alternating current flow in the presence of the magnetic field is transferred to the lattice of the conductor. This force produces an ultrasonic wave (with the same frequency as the eddy currents) which propagates through the material. In electromagnetic acoustic generation, the electromagnetic conversion takes place directly within the eddy current skin depth. No mechanical coupling to the body is needed because the metal surface is its own transducer. Similarly, the reception at an EMAT takes place in a reciprocal way.

Various configurations of the eddy current coil may be used, along with different directions of the magnetic field, to produce a variety of ultrasonic wave modes with unique properties in addition to the conventional longitudinal and shear waves. In conductors that are ferromagnetic, a second force, magnetostriction, is added to the Lorentz force. This makes ferromagnetic materials particularly suitable for sensitive EMAT inspection. The absence of a couplant thus makes it possible to design transducers that operate at elevated temperatures and allows rapid scanning. In addition, the operating characteristics of EMATs can be reproduced from one unit to another very easily making them potentially useful as ultrasonic standards.

SUMMARY OF THE INVENTION

Accordingly, one aspect of the present invention is drawn to a method of examining a ductile iron casting to determine a percent of nodularity present in the casting using an electromagnetic acoustic transducer (EMAT) system. The method comprises providing first and second EMATs arranged in pitch-catch mode on opposite sides of the casting at a selected location. A thickness, t, of the casting is measured at said location. The first EMAT is energized to create and send an ultrasonic zero degree shear wave pulse through the casting towards the second EMAT, the ultrasonic zero degree shear wave pulse experiencing several internal reflections within the casting. The ultrasonic zero degree shear wave pulse is received at the second EMAT and the time required for the ultrasonic pulse to travel through twice the thickness, t, of the casting at said location is measured. The shear wave velocity, $V_{SHEAR}$, of the ultrasonic zero degree shear wave pulse through the casting at said location is calculated according to the relationship $V_{SHEAR} = (2 \times t) / T_{DELTA}$, and the degree of nodularity in the casting is determined from a pre-established relationship between the calculated shear wave velocity, $V_{SHEAR}$, and the percent of nodularity for ductile cast iron.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 5 is a schematic representation of the ultrasonic, zero degree shear wave pulses propagating through a casting being inspected by the method of the present invention, showing multiple internal reflections;

FIG. 6 is a graphical representation of a typical oscilloscope trace showing the multiple internal reflections of FIG. 5, and which defines the various time delays $T_{DELAY1}$, $T_{DELAY2}$, and the net transit time $T_{DELTA}$; and FIG. 7 is a tabulation of a comparison of test data on three sample castings including time-of-flight, thickness, and calculated velocity values using the method of the present invention as compared to previous ultrasonic immersion test values made and provided by the foundry that supplied the sample castings.

DESCRIPTION OF THE PREFERRED EMBODIMENT

Figure 3:
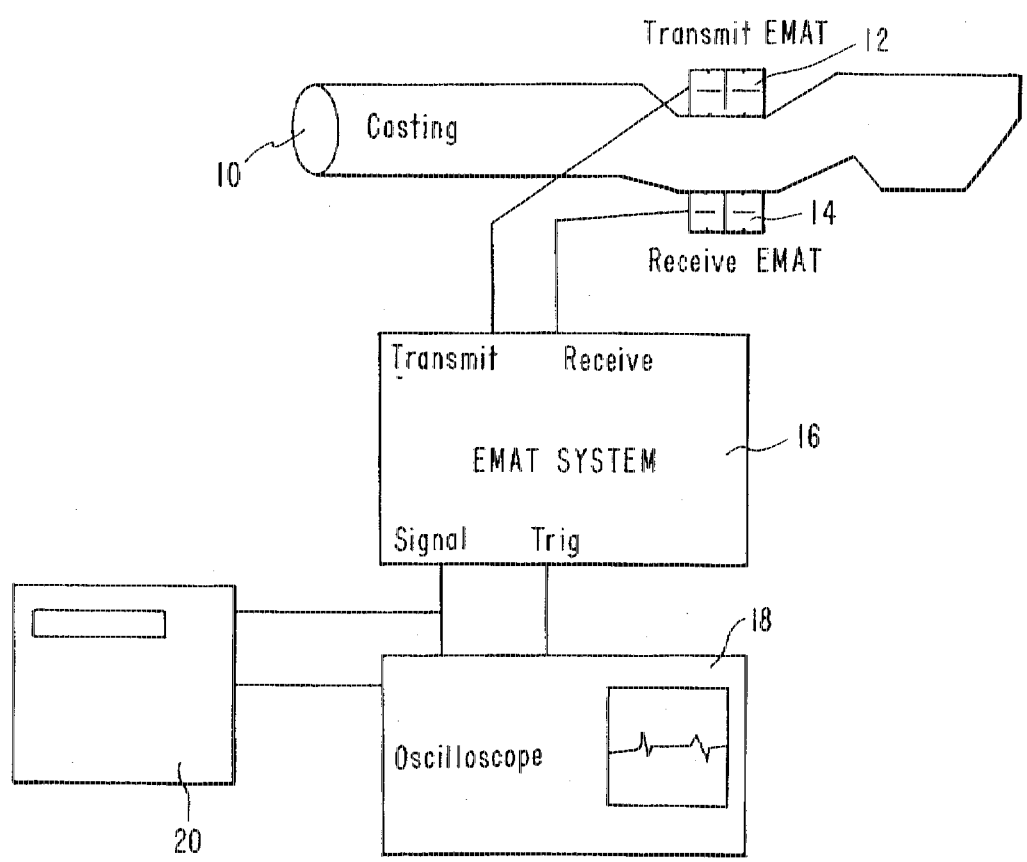
FIG. 3 is a schematic representation of an EMAT system used in the practice of the present invention.

Referring to the drawings generally, wherein like numerals designate the same of functionally similar elements throughout the several drawings, and to FIG. 3 in particular, there is shown a block diagram of an electromagnetic acoustic transducer (EMAT) system used to examine ductile iron castings to determine a percent of nodularity present in the casting. To inspect a ductile iron casting 10 for nodularity, transmit and receive EMATs 12, 14 respectively, are provided on opposite sides of the casting 10. The first and second EMATs 12, 14 are arranged in a pitch-catch mode and are connected to an EMAT system 16 of known design, used to create, send, and receive ultrasonic, zero degree shear wave pulses to and from the casting 10. The output from the EMAT system 16 is provided to an oscilloscope 18 also of known design. To accurately determine the velocity of the ultrasonic shear wave pulse transmitted through the casting 10, a measurement of thickness, t, of the casting 10 must be made at the particular location where transmission of the ultrasonic shear wave pulse is to occur. The thickness measurement can be made by any type of known means, such as by using a micrometer and manually measuring the thickness, t, or through use of a linear variable differential transducer (LVDT), or by use of a laser interferometry system. Regardless of the particular measurement means or technique used, it is important to a successful practice of the present invention that an accurate thickness is determined, since the velocity of the ultrasonic shear wave pulse transmitted through the casting 10 is directly calculated using the thickness, t.

The first EMAT 12 is energized to create and send an ultrasonic zero degree shear wave pulse through the casting 10 towards the second EMAT 14 at the given location. The ultrasonic pulse will experience several internal reflections within the casting 10. The ultrasonic zero degree shear wave pulse is received at the second EMAT 14 after several reflections, and the absolute time delays for both second, $T_{DELAY1}$, and third, $T_{DELAY2}$, multiple reflections are used to determine the time, $T_{DELTA}$, required for the ultrasonic zero degree shear wave pulse to travel through twice the thickness, t, of the casting 10 at the given location. The ultrasonic shear wave velocity, $V_{SHEAR}$, of the ultrasonic pulse through the casting 10 is determined by dividing twice the thickness of the casting 10 at the location by $T_{DELTA}$. Once the ultrasonic shear wave velocity, $V_{SHEAR}$, is obtained, a percent of nodularity of the casting 10 can be determined from a pre-established relationship between calculated ultrasonic shear wave velocity $V_{SHEAR}$ and the percent of nodularity for the material of interest, in this case ductile cast iron.

Figure 1:
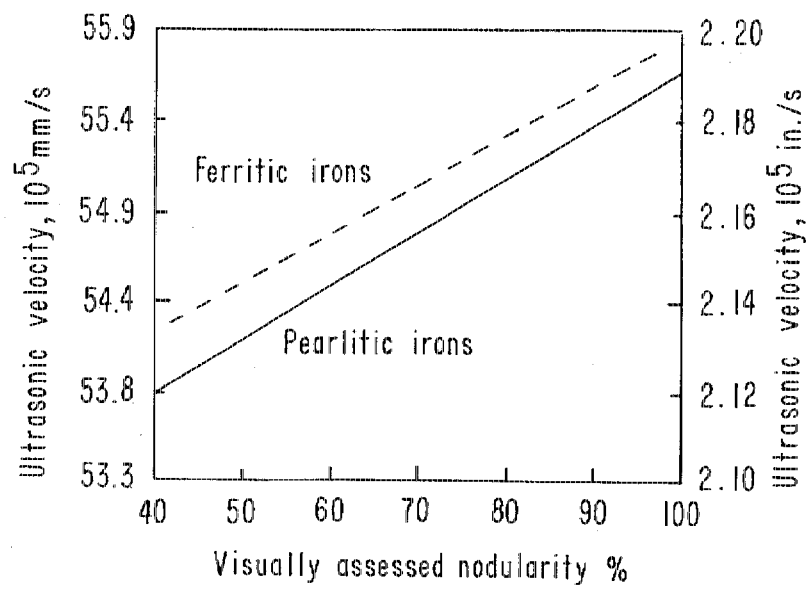
FIG. 1 is a known graphical representation of the variation of ultrasonic velocity versus visually assessed nodularity in ductile iron castings, as disclosed in the *Metals Handbook*, Vol. 17, supra.
Figure 2:
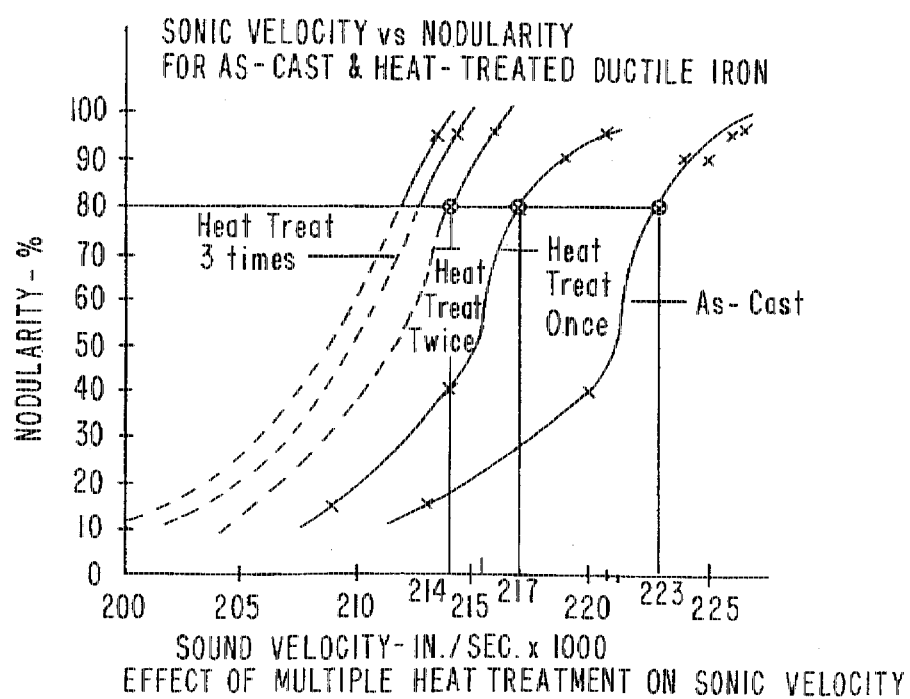
FIG. 2 is a known graphical representation of the longitudinal velocity/nodularity relationship in ductile iron castings, as disclosed in H. E. Henderson's article "Ultrasonic Velocity Techniques for Quality Assurance of Ductile Iron Castings", supra.

It is recognized that the calculated ultrasonic shear wave velocity, $V_{SHEAR}$, may be used in various ways to determine the percent of nodularity of the casting 10. By way of example and not limitation, the pre-established relationship may be a pre-established graphical relationship as shown in FIGS. 1 and 2 of the present disclosure. Similarly, the step of determining the percent of nodularity in the casting may comprise using the calculated ultrasonic shear wave velocity $V_{SHEAR}$ an entry value in a programmable look-up table which relates the calculated ultrasonic shear wave velocity, $V_{SHEAR}$, with values of the percent of nodularity for the material of interest. Interpolations using linear or other known methods can be used to take care of intermediate values not precisely found in such a look-up table. Similarly, the calculated ultrasonic shear wave velocity, $V_{SHEAR}$, may be used as an entry value used in calculation procedures using an empirically derived equation which relates, $V_{SHEAR}$, with the percent of nodularity of the material of interest. For any of the above, suitable calculation and display means well known to those skilled in the art and advantageously microprocessor based, would be provided as schematically represented at 20 in FIG. 3.

In order to evaluate the feasibility of using EMATs to determine nodularity, three sample castings were obtained from a foundry. Zero degree shear wave EMATs were constructed and used to measure ultrasonic shear wave velocities in the samples. The results of these tests were then compared to ultrasonic longitudinal wave velocity measurements taken by the foundry's existing, immersion ultrasonic testing station currently used in production.

The three sample castings were ends for a tie rod assembly, and were numbered #1, #2, and #4. The castings had two flat areas that were located on opposite sides (i.e. parallel surfaces). This feature was designed specifically to simplify velocity measurements by minimizing geometric effects.

Figure 4:
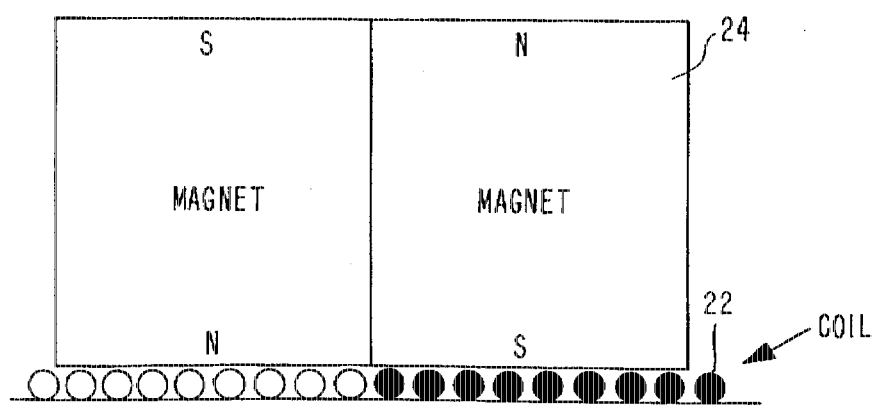
FIG. 4 is a schematic representation of an EMAT coil assembly used to produce zero degree shear waves in the practice of the present invention.

Due to the size of the castings that were evaluated, relatively small transmit and receive EMATs 12, 14 respectively, were required, having a footprint of approximately ⅜"×⅜". Each EMAT's coil 22 was a rectangular, symmetrical coil (FIG. 4) and was used to produce ultrasonic zero degree shear waves. The coil 22 of the receiving EMAT 14 was wound using smaller gauge wire than that of the coil 22 of the transmitting EMAT 12. This improved sensitivity and was especially important since optimum magnets were not utilized. The magnets 24 used were cylindrical with one placed atop each of the rectangular coils 22, and the EMATs 12, 14 were placed on opposing sides of the casting 10 and operated in a pitch-catch mode. The EMATs 12, 14 were connected to a single-channel, multi-frequency, tunable EMAT system 16 used specifically for development purposes. The EMAT coils themselves were operated at approximately 1.3 MHz and the resulting signals were monitored using a Tektronix TDS 460 Digital Oscilloscope 18. This instrument was used due to its capability for signal averaging as well as for its ability to make precise time-of-flight measurements.

The absolute delay time was measured for both the second ($T_{DELAY1}$) and third, ($T_{DELAY2}$) multiple reflections observed for each casting 10. These values were then mathematically subtracted in order to obtain the time required for the signals to travel through twice the thickness, t, of each sample casting 10 ($T_{DELTA}$). The subtraction can be done either automatically using a computer algorithm (autocorrelation) or by manual calculation. The shear wave velocity was then calculated using the following formula: $V_{SHEAR}=(2 \times t)/T_{DELTA}$. FIGS. 5 and 6 of the present disclosure illustrate transmission of such signals into the casting 10, and how all time measurements were made relative to the second threshold crossing of each signal. In the particular tests identified above, the thickness of each casting 10 was measured using micrometers. Three separate readings were taken for each casting 10 at the general location where the EMATs 12, 14 were placed. An average of the three thickness measurements was used to determine the ultrasonic zero degree shear wave velocity.

FIG. 7 is a chart which summarizes the time-of-flight, thickness, and calculated ultrasonic zero degree shear wave velocity data for each sample casting. Also included in this chart are ultrasonic longitudinal wave velocities provided by the foundry which supplied sample castings 10.

Theoretically, any changes observed in longitudinal wave velocity should also be observed in shear wave velocities. This statement assumes that velocity variations are primarily a result of variations in Young's modulus of elasticity, E. The two equations below show the relationship between ultrasonic longitudinal wave and shear wave velocities in a material and Young's modulus of elasticity, E, for the material:

$$V_{LONGITUDINAL} = \sqrt{\frac{E(1-\mu)}{\rho(1+\mu)(1-2\mu)}}$$

$$V_{SHEAR} = \sqrt{\frac{E1}{\rho 2(1+\mu)}}$$

where:

$\mu$=Poisson's ratio $\rho$=density of the material.

Therefore, assuming constant density, the amount of change in both the ultrasonic longitudinal wave and shear wave velocity is proportional to the square root of Young's modulus.

As will be apparent from a review of FIG. 7, the ultrasonic shear wave velocities do not show a large variation. It can thus be assumed that these sample castings have similar microstructure and degree of nodularity. H. E. Henderson's paper, supra, discloses that the ultrasonic longitudinal wave velocity can change as much as 5% when comparing nodularity of 15% with 100%. The shear wave data from the three sample castings 10 represents only a 0.7% variation in velocity. This change would represent a span of approximately 4% to 17% variation in percent nodularity according to Henderson's "as-cast" data for longitudinal velocity (FIG. 2 of the present disclosure). The longitudinal wave velocity data provided by the foundry likewise indicated a small change in velocity. These values varied by approximately 0.3%.

The primary advantage of the invention is that it is an absolute and objective method which eliminates operator subjectivity. The most common method of nodularity measurement in ductile iron castings is the metallographic technique, where a sample is sectioned and polished to reveal the microstructure. This is a destructive technique, however. Additionally, because the microscopic estimation of nodularity is a subjective measurement, involving a judgement call by a technician comparing a microstructure to an ASTM standard, ultrasonic velocity measurements or other absolute nondestructive examination methods provide a better guide to some properties, provided that the matrix remains constant.

Another significant advantage to the invention is that an absolute measurement of nodularity can be obtained without the use of a fluid coupling medium as required with conventional ultrasonic methods. These methods typically require the sample to be submerged in a fluid filled tank where the ultrasonic energy is coupled into the part. The prior art ultrasonic velocity process is slow, inherently messy, subject to associated couplant errors, and can promote surface corrosion.

While specific embodiments of the invention have been shown and described in detail to illustrate the application of the principles of the invention, it will be understood that the invention may be embodied otherwise without departing from such principles. All such embodiments have been deleted herein for the sake of conciseness and readability but properly fall within the scope of the following claims.

We claim:

1. A method of examining a ductile iron casting using an electromagnetic acoustic transducer (EMAT) system to determine a percent of nodularity present in the casting, comprising the steps of:

providing first and second EMATs arranged in pitch-catch mode on opposite sides of the casting at a selected location;

measuring a thickness, t, of the casting at said location;

energizing the first EMAT to create and send an ultrasonic zero degree shear wave pulse through the casting towards the second EMAT at said location, the ultrasonic zero degree shear wave pulse experiencing several internal reflections within the casting;

receiving the ultrasonic shear wave pulse at the second EMAT and measuring the absolute delay time for both second, $T_{DELAY1}$, and third, $T_{DELAY2}$, multiple reflections and mathematically subtracting $T_{DELAY1}$ from $T_{DELAY2}$ to determine a time, $T_{DELAY}$, representative of the time required for the ultrasonic pulse to travel through twice the thickness, t, of the casting at said location;

calculating the shear wave velocity, $V_{SHEAR}$, of the ultrasonic zero degree shear wave pulse through the casting at said location according to the relationship $$V_{SHEAR} = (2 \times t)/T_{DELTA}; \text{ and}$$

determining a percent of nodularity in the casting from a pre-established relationship between the calculated shear wave velocity, $V_{SHEAR}$, and the percent of nodularity for ductile cast iron.

2. The method according to claim 1, further comprising the step of using a micrometer to measure the thickness, t, of the casting.

3. The method according to claim 1, further comprising the step of using a linear variable differential transducer to measure the thickness, t, of the casting.

4. The method according to claim 1, further comprising the step of using a laser interferometry system to measure the thickness, t, of the casting.

5. The method according to claim 1, including the step of operating the first and second EMATs at a frequency of approximately 1.3 MHz.

6. The method according to claim 1, wherein the step of determining the percent of nodularity in the casting comprises using a pre-established graphical relationship between the calculated shear wave velocity, $V_{SHEAR}$, and the percent of nodularity for ductile cast iron.

7. The method according to claim 1, wherein the step of determining the percent of nodularity in the casting comprises using the calculated shear wave velocity, $V_{SHEAR}$, as an entry value to a programmable look-up table which relates the calculated shear wave velocity, $V_{SHEAR}$, with corresponding values of percent of nodularity for ductile cast iron.

8. The method according to claim 1, wherein the step of determining the percent of nodularity in the casting comprises using the calculated shear wave velocity, $V_{SHEAR}$, as an entry value to an empirically derived equation which relates the calculated shear wave velocity, $V_{SHEAR}$, with corresponding values of percent of nodularity for ductile cast iron.

* * * * *